United States Patent [19]

Hakamata et al.

[11] Patent Number: 5,053,248
[45] Date of Patent: Oct. 1, 1991

[54] METHOD FOR FIXING ON CLOTH SEMICONDUCTOR MATERIAL WITH A CONTACT-POTENTIAL DIFFERENCE, AND CLOTH BEARING SUCH SEMICONDUCTOR MATERIAL

[75] Inventors: Shigeya Hakamata; Takumi Kurihara; Shinichiro Ishigaki; Hiroshi Fuziyasu, all of Shizuoka, Japan

[73] Assignee: Daiwa Senko Company, Ltd., Hamamatsu, Japan

[21] Appl. No.: 253,799

[22] Filed: Oct. 5, 1988

[51] Int. Cl.$^5$ ............................................. B05D 5/12
[52] U.S. Cl. ...................................... 427/58; 427/123
[58] Field of Search .............. 428/195, 196, 206, 207, 428/208, 209, 260, 253, 254, 922, 331, 323; 427/58, 123; 156/78, 277, 278, 279

[56] References Cited

U.S. PATENT DOCUMENTS 4,247,594  1/1981  Shea et al. ............................ 427/58
4,913,930  4/1990  Getson ................................. 427/58

Primary Examiner—James J. Bell
Attorney, Agent, or Firm—Jordan & Hamburg

[57] ABSTRACT

A cloth having a semiconductor material deposited thereon is capable of producing a contact-potential difference when contacted with the skin for removing stiffness and recovering muscles from fatigue. The cloth is produced by pulverizing a contact-potential difference-generating substance such as germanium or silicon into a particle size of smaller than 200–250 $\mu$, adding 4–100 g of the pulverized substance to 1 kg of a non-conducting organic polymer resin liquid or printing color paste, and printing or coating the mixture onto a woven or knit fabric.

12 Claims, 1 Drawing Sheet

METHOD FOR FIXING ON CLOTH SEMICONDUCTOR MATERIAL WITH A CONTACT-POTENTIAL DIFFERENCE, AND CLOTH BEARING SUCH SEMICONDUCTOR MATERIAL

TECHNICAL FIELD OF THE INVENTION

This invention relates to a method for fixedly depositing on cloth a semiconductor material capable of generating a contact-potential difference, and cloth having such a semiconductor material deposited thereon by the use of a color paste or resin liquid containing the semiconductor component in a specific concentration. The resulting cloth is useful for healthy clothes or other healthy goods.

BACKGROUND OF THE INVENTION

Heretofore, various healthy goods have been proposed. For example, there have been proposed adhesive plasters using magnetic material or granular semiconductor material (germanium, silicon or the like) of red bean size for giving magnetic stimulation or effects similar to finger-pressure therapy.

In consideration of the contact-potential difference which is exhibited by germanium and silicon upon contact with the human body, the present invention contemplates to facilitate the deposition of pulverized particles of these materials on cloth and the setting of the concentration of the semiconductor material when combining the same with a printing color paste or an organic polymer resin liquid, while diversifying the pole of potential difference, thereby to provide effective healthy clothes or healthy goods.

Although proposals of this sort have been made before, they all remain in the sphere of mere conception, without clarifying a particular form of the semiconductor material, a particular form of other material for fixedly depositing the same on an object article, or a particular method for fixedly depositing the same on an object article. Therefore, there have been a number of problems to be solved before reducing the concepts to practice.

SUMMARY OF THE INVENTION

The present invention is proposed in an attempt to solve the above-mentioned problems, and has as its object the provision of a method for fixedly depositing on cloth finely pulverized particles of a semiconductor material with a contact-potential difference by adding the same to a printing color paste or an organic polymer resin liquid, for providing healthy clothes and goods.

The gist of the invention resides in pulverizing a substance capable of producing a contact-potential difference into a particle size smaller than 200–250$\mu$, and printing or coating the same on cloth by the use of a nonconducting organic polymer resin liquid or a printing color paste.

DESCRIPTION OF THE PREFERRED EMBODIMENTS

Figure 1A:
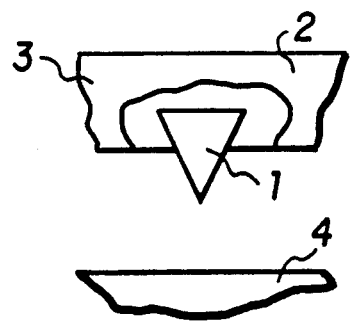
FIGS. 1a to 1c are illustrations on an enlarged scale of the conditions of the semiconductor material and skin before and after contact with each other, showing at FIG. 1a the condition before contact, at FIG. 1b the condition at the time of contact, and at FIG. 1c the condition after contact.

Useful for the cloth are various woven and knit fabrics of natural and synthetic fibers such as cotton, polyester/cotton and polyester.

Examples of the organic polymer resin liquid or printing color paste useful in the present invention include resin liquids for permanent treatment, polishing resin liquids, and pigmented color pastes and the like. Taking into consideration the contact-potential difference and the field strength as a semiconductor material, the printing color paste or the organic polymer resin liquid to be used in the present invention is preferred to be an insulator or to have values similar to an insulator. In this regard, an acrylic or epoxy resin is preferred.

The contact-potential difference producing material to be added, for instance, germanium, silicon or the like, is preferred to be refined material of high purity, and mixed with water before adding the same to the printing color paste or organic polymer resin liquid. Examples of applicable semiconductor material include, in addition to the above-mentioned germanium and silicon, silicon carbide, germanium-silicon alloys and the like, which may be used singly or in combination. Indium antimonide is unsuitable for application to the human body in view of its toxicity. The finely pulverized particles of the semiconductor material are preferred to have a shape with an acute angle rather than a spherical or elliptic shape in consideration that they are pressed on for finger pressure effect when used to improve stiff shoulders and recovery of muscular strength. In this connection, it has been revealed that grain sizes in the range of 200–150$\mu$ are more effective and better in productivity.

It is possible to add the semiconductor material to the printing color paste or the organic polymer resin liquid in a ratio of 4–100 g to 1 kg. Particularly, the semiconductor material is preferred to be added in an amount of 5–50 g g because the effects on health, recovery of muscular strength and stiff shoulders will become insufficient if its content is less than 49 g and the mass production will be disadvantageously hindered by variations of fluidity of the printing color paste or the organic polymer resin liquid if its content is larger than 100 g.

Turning now to an example of the method for fixedly depositing the semiconductor material on cloth, a printing color paste or an organic polymer resin liquid, which contains germanium, silicon or the like, is applied on or impregnated into cellulose base fabric, for instance, cotton broad, mercerized cloth or the like, followed by drying at 100° C. and, if necessary, a curing treatment for 3 minutes at 150° C. After depositing the semiconductor material in this manner, the cloth is cut into a suitable shape depending upon the purpose of use to obtain a final product of a desired shape.

This method of deposition of a semiconductor material on cloth is effective since it can be carried out by an ordinary textile treating method.

EXAMPLE 1

30 g of refined and finely pulverized germanium (99.999% purity) and 30 g of silicon (99.999% purity) were mixed with 100 cc of water, and admixed with a pigment resin (an acrylate copolymer) to make a total amount of 1 kg. The resulting mixture was stirred well to disperse germanium and silicon uniformly.

These semiconductor materials were printed on cotton broad by the use of a 120 mesh screen, and, after drying and curing, the cloth was cut into a suitable size and an adhesive tape was bonded on the non-printed side to obtain a final product which resembled an adhesive plaster.

EXAMPLE 2

10 g of New Laqutimine Yellow FL2R, 5 g of New Laqutimine Blue FLTR, 25 g of germanium and 60 g of silicon were mixed in 100 cc of water, and lactimine binder was added to make a total amount of 1 kg.

These semiconductor materials were printed on cotton knit elastic fabric by the use of a 120 mesh screen, and, after drying and curing, it was cut into a suitable size and the non-printed side was attached to a band using elastic substrate cloth (Spuntex, knit fabric etc.) through a hook and loop fastener to obtain a final product.

EXAMPLE 3

50 g of a cellulose-reacting type resin, 10 g of complex metal salt-base catalyst, 10 g of polyolefinic derivative, 20 g of germanium and 60 g of silicon were mixed adding water to make a total amount of 1 kg.

These semiconductor materials were impregnated into cotton sheeting dyed in solid color, by the use of a mangle of ordinary dye adjustment equipment (wet pick up 80%), followed by drying in a drier and curing in a baking machine.

EXAMPLE 4

30 g of germanium, 30 g of silicon and 100 cc of water were mixed with an acrylate copolymer and a foaming agent to make a total amount of 1 kg.

These semiconductor substances were printed in spots (with a diameter of about 5-10 mm) with a total printed area of about 50%, and, after drying, subjected to a curing treatment to foam the spots into a raised state.

The semiconductor material which is deposited on cloth acts on the human body in the manner explained below.

When the human body and germanium are brought into contact with each other, a potential difference of about 0.1 V is produced therebetween. If the mean distance d between the human body and germanium is 1 $\mu$m, the field strength is $E_1 = 0.1$ V/1 $\mu$m $= 0.1/10^{-4} = 10^3$ V/cm. On the other hand, it is dangerous if one approaches a cable of 10,000 V up to a distance of 1 m where the field strength is $E_2 = 10^4$ V/$10^2$ cm $= 100$ V/cm.

Comparing $E_1$ and $E_2$, one will see that $E_1/E_2 = 10$-100 when d is 0.1-1 $\mu$m. Thus, the contact electric field is very strong and considered to have effects of improving stiff shoulders and recovering muscular strength.

Figure 1B:
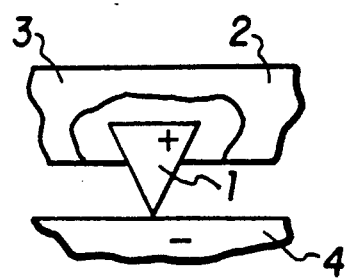
Figure 1C:
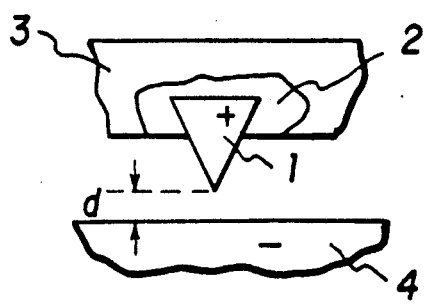

Besides, the small current which flows at the time of contact is considered to have an effect of stimulating the skin. FIGS. 1a to 1c show the conditions of germanium and skin before and after the contact. In the Figures, element 1 is a semiconductor material, element 2 is an organic polymer resin liquid, element 3 is a substrate cloth and element 4 is skin. As the two contacting parts are separated, an electric field is produced with a strength of $E_1 = 10^3$-$10^4$ V/cm.

These effects are also produced by the semiconductor bearing cloth when it is provided with an adhesive tape on one side in the fashion of adhesive plaster and bonded on a shoulder or hip, improving a stiffened shoulder or recovering muscular strength. When elastic substrate cloth is used and the semiconductor plaster is applied pressingly around an elbow or knee, it has an effect of recovering the applied portion from fatigue. If the semiconductor material is applied to suitable portions of under wear or a bathrobe for contact with neck, wrist or shoulder portions, the effect of recovering the contacting portions from fatigue is also produced. If the semiconductor material is printed in a pattern of spots or staggered check and in a raised form by the use of a foaming agent, effects similar to finger pressure therapy are also produced.

Figure 2:
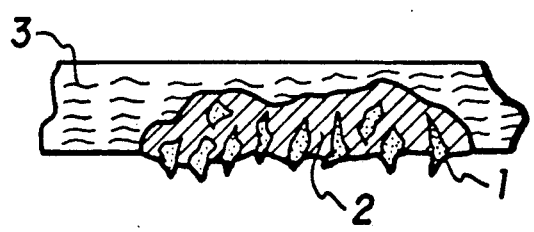
FIG. 2 is an enlarged partly sectioned view of the cloth on which the semiconductor material is deposited.

FIG. 2 shows on an enlarged scale the condition of the semiconductor material which is deposited on cloth by the method of the present invention. The fore ends of the semiconductor particles which are in contact with the skin are pointed at acute angles which obviously impose a stronger stimulative pressure as compared with particles of flat or spherical shapes.

The organic polymer resin liquid 2 which fixes the semiconductor material 1 on cloth is desired to have an insulating property to produce a greater contact-potential difference.

The results of experiments proved extremely high durability including high washing durability of grade 4-5.

It has also been found that the pointed ends of the semiconductor material which contact the skin are exposed gradually as the insulating material over and around pointed ends are removed by repeated washing, thereby maintaining or rather improving the effects of the semiconductor bearing cloth.

As compared with a case using germanium grains which contact the skin 4 point-wise, the cloth according to the present invention maintains surface-wise contact which is effective for making contact near an effective point on the human body even when the effective point is unknown.

A contact-potential difference is produced when the semiconductor material 1 is brought into contact with the skin 4.

Namely, current flows upon contact, positively charging one of the contacting parts while negatively charging the other part as shown particularly in FIGS. 1b and 1c.

The same conditions apply even when the two parts are separated to a slight degree.

As clear from the foregoing description, the present invention provides a method for fixedly depositing on cloth a contact-potential difference producing substance in an appropriate manner, and a semiconductor deposited cloth which can be easily processed into a form suitable for end use, greatly contributing to the recovery and promotion of health.

What is claimed for patent is:

1. A method for fixing on cloth a semiconductor material capable of producing a contact-potential difference, comprising pulverizing a contact-potential difference-generating substance into a particle size smaller than 200-250$\mu$, mixing said pulverized substance with a component selected from the group consisting of a non-conducting organic polymer resin liquid and a printing color paste to therefore form a mixture, and applying said mixture onto said cloth.

2. A method for fixing on cloth a semiconductor material capable of generating a contact-potential difference according to claim 1, further comprising adding 4-100 g of said contact-potential difference-generating substance to 1 kg of said non-conducting organic polymer resin liquid or printing color paste prior to applying onto said cloth.

3. A method for fixing on cloth a semiconductor material capable of generating a contact-potential difference according to claim 1, wherein said contact-potential diference-generating substance comprises pulverized micro particles having surfaces forming acute angles.

4. A method for fixing on cloth a semiconductor material capable of generating a contact-potential difference according to claim 1, comprising, after applying onto said cloth, drying said semiconductor substance and curing said semiconductor substance for three minutes at 150° C.

5. A method for fixing on cloth a semiconductor material capable of producing a contact-potential difference according to claim 1, wherein said contact-potential difference-generating substance is selected form the group consisting of germanium, silicon, silicon carbide, germanium-silicon alloys and mixtures thereof.

6. A method for fixing on cloth a semiconductor material capable of producing a contact-potential difference according to claim 1, wherein said applying step comprises printing said mixture onto said cloth.

7. A method for fixing on cloth a semiconductor material capable of producing a contact-potential difference according to claim 1, wherein said applying step comprises coating said mixture onto said cloth.

8. A method for fixing on cloth a semiconductor material capable of producing a contact-potential difference according to claim 1, wherein said cloth is selected from the group consisting of woven fabric and knit fabric.

9. A method for fixing on cloth a semiconductor material capable of producing a contact-potential difference according to claim 1, further comprising, after applying onto said cloth, cutting said cloth to a desired size and shape, and bonding said cut cloth to an elastic substrate cloth.

10. A method for fixing on cloth a semiconductor material capable of producing a contact-potential difference according to claim 1, further comprising, after applying onto said cloth, bonding said cloth to an adhesive tape.

11. A method for fixing on cloth a semiconductor material capable of producing a contact-potential difference according to claim 1, further comprising, prior to applying onto said cloth, adding a foaming agent to said pulverized substance.

12. A method for fixing on cloth a semiconductor material capable of producing a contact-potential difference according to claim 1, wherein said applying step comprises impregnating said cloth with said mixture.

* * * * *